(12) United States Patent
Tyavanagimatt et al.

(10) Patent No.: US 9,889,119 B2
(45) Date of Patent: Feb. 13, 2018

(54) AMORPHOUS TECOVIRIMAT PREPARATION

(71) Applicant: SIGA TECHNOLOGIES, INC., Corvallis, OR (US)

(72) Inventors: Shanthakumar R. Tyavanagimatt, Corvallis, OR (US); N K Peter Samuel, Corvallis, OR (US); Joseph Paz, Corvallis, OR (US); Ying Tan, Walnut Creek, CA (US); Dennis E. Hruby, Albany, OR (US)

(73) Assignee: SIGA TECHNOLOGIES, INC., Corvallis, OR (US)

( * ) Notice: Subject to any disclaimer, the term of this patent is extended or adjusted under 35 U.S.C. 154(b) by 0 days.

(21) Appl. No.: 15/498,787

(22) Filed: Apr. 27, 2017

(65) Prior Publication Data

US 2017/0224661 A1    Aug. 10, 2017

Related U.S. Application Data

(62) Division of application No. 14/903,083, filed as application No. PCT/US2014/046340 on Jul. 11, 2014, now Pat. No. 9,670,158.

(60) Provisional application No. 61/586,240, filed on Jul. 19, 2013.

(51) Int. Cl.
| | |
|---|---|
| *C07D 209/70* | (2006.01) |
| *A61K 31/4035* | (2006.01) |
| *A61K 9/16* | (2006.01) |
| *A61K 47/38* | (2006.01) |
| *A61K 47/32* | (2006.01) |
| *A61K 47/10* | (2017.01) |

(52) U.S. Cl.
CPC ........ *A61K 31/4035* (2013.01); *A61K 9/1694* (2013.01); *A61K 47/10* (2013.01); *A61K 47/32* (2013.01); *A61K 47/38* (2013.01); *C07D 209/70* (2013.01)

(58) Field of Classification Search
CPC .................................................... C07D 209/70
USPC ........................................................ 548/420
See application file for complete search history.

(56) References Cited

U.S. PATENT DOCUMENTS

| | | |
|---|---|---|
| 2001/0053778 A1 | 12/2001 | Hoover et al. |
| 2007/0003516 A1 | 1/2007 | Almond et al. |
| 2008/0004452 A1 | 1/2008 | Jordan et al. |
| 2011/0236434 A1 | 9/2011 | Tyavanagimatt et al. |

OTHER PUBLICATIONS

International Search Report issued in PC/US14/46340 dated Oct. 16, 2015.
Written Opinion of the International Searching Authority issued in PCT/US14/46340 dated Oct. 16, 2014.
International Preliminary Report issued in International Application No. PCT/US2014/046340 dated Jan. 19, 2016.

*Primary Examiner* — Matthew Coughlin
*Assistant Examiner* — Sagar Patel
(74) *Attorney, Agent, or Firm* — Charles C. Achkar; Ostrolenk Faber LLP.

(57) ABSTRACT

Disclosed are methods for the preparation of amorphous N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide for the treatment or prophylaxis of viral infections and diseases associated therewith, particularly those viral infections and associated diseases caused by the orthopoxvirus. Also disclosed are methods for the preparation of amorphous solid dispersion of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

11 Claims, 1 Drawing Sheet

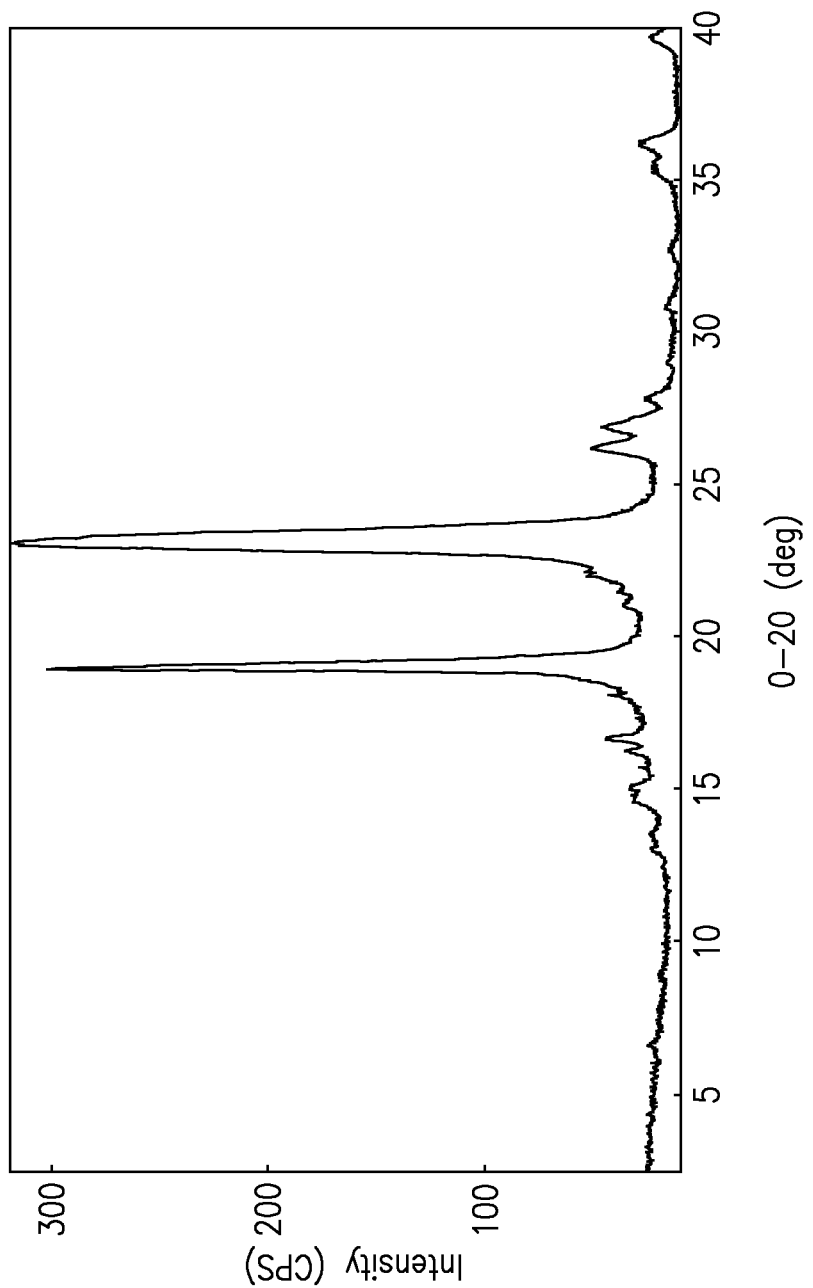

AMORPHOUS TECOVIRIMAT PREPARATION

This application is a divisional of U.S. application. Ser. No. 14/903,083 filed Jan. 6, 2016. which is a §371 National Phase Application of International Application No. PCT/US2014/046340 filed Jul. 11, 2014, which claims priority to U.S. Provisional Patent Application Ser. No. 61/856,240 filed Jul. 19, 2013, which is hereby incorporated herein by reference in its entirety and for all purposes.

STATEMENT REGARDING FEDERALLY SPONSORED RESEARCH OR DEVELOPMENT

This invention was made with U.S. government support under Contract No.: HHSO100201100001C awarded by the Biomedical Advanced Research and Development Authority (BARDA). The US government has certain rights in this invention.

FIELD OF THE INVENTION

Described herein are methods for the preparation of amorphous Tecovirimat for the treatment or prophylaxis of viral infections and diseases associated therewith, particularly those viral infections and associated diseases caused by the orthopoxvirus. Tecovirimat, with a proprietary name of ST-246®, has a chemical name of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

BACKGROUND OF THE INVENTION

The *Orthopox* genus (Orthopoxviridae) is a member of the Poxviridae family and the Choropoxivirinae subfamily. The genus consists of numerous viruses that cause significant disease in human and animal populations. Viruses in the *orthopox* genus include cowpox, monkeypox, vaccinia, and variola (smallpox), all of which can infect humans.

The smallpox (variola) virus is of particular importance. Recent concerns over the use of smallpox virus as a biological weapon have underscored the necessity of developing small molecule therapeutics that target orthopoxviruses. Variola virus is highly transmissible and causes severe disease in humans resulting in high mortality rates (Henderson et al. (1999) JAMA. 281:2127-2137). Moreover, there is precedent for use of variola virus as a biological weapon. During the French and Indian wars (1754-1765), British soldiers distributed blankets used by smallpox patients to American Indians in order to establish epidemics (Stern, E. W. and Stern, A. E. 1945. The effect of smallpox on the destiny of the Amerindian. Boston). The resulting outbreaks caused 50% mortality in some Indian tribes (Stern, E. W. and Stern, A. E.). More recently, the Soviet government launched a program to produce highly virulent weaponized forms of variola in aerosolized suspensions (Henderson, supra). Of more concern is the observation that recombinant forms of poxvirus have been developed that have the potential of causing disease in vaccinated animals (Jackson et al. (2001) J. Virol., 75:1205-1210).

The smallpox vaccine program was terminated in 1972; thus, many individuals are no longer immune to smallpox infection. Even vaccinated individuals may no longer be fully protected, especially against highly virulent or recombinant strains of virus (Downie and McCarthy. (1958) J Hyg. 56:479-487; Jackson, supra). Therefore, mortality rates would be high if variola virus were reintroduced into the human population either deliberately or accidentally.

Variola virus is naturally transmitted via aerosolized droplets to the respiratory mucosa where replication in lymph tissue produces asymptomatic infection that lasts 1-3 days. Virus is disseminated through the lymph to the skin where replication in the small dermal blood vessels and subsequent infection and lysis of adjacent epidermal cells produces skin lesions (Moss, B. (1990) Poxviridae and Their Replication, 2079-2111. In B. N. Fields and D. M. Knipe (eds.), Fields Virology. Raven Press, Ltd., New York). Two forms of disease are associated with variola virus infection; variola major, the most common form of disease, which produces a 30% mortality rate and variola minor, which is less prevalent and rarely leads to death (<1%). Mortality is the result of disseminated intravascular coagulation, hypotension, and cardiovascular collapse, that can be exacerbated by clotting defects in the rare hemorrhagic type of smallpox (Moss, supra).

A recent outbreak of monkeypox virus underscores the need for developing small molecule therapeutics that target viruses in the orthopox genus. Appearance of monkeypox in the US represents an emerging infection. Monkeypox and smallpox cause similar diseases in humans, however mortality for monkeypox is lower (1%).

Vaccination is the current means for preventing orthopox virus disease, particularly smallpox disease. The smallpox vaccine was developed using attenuated strains of vaccinia virus that replicate locally and provide protective immunity against variola virus in greater than 95% of vaccinated individuals (Modlin (2001) MMWR (Morb Mort Wkly Rep) 50:1-25). Adverse advents associated with vaccination occur frequently (1:5000) and include generalized vaccinia and inadvertent transfer of vaccinia from the vaccination site. More serious complications such as encephalitis occur at a rate of 1:300,000, which are often fatal (Modlin, supra). The risk of adverse events is even more pronounced in immunocompromised individuals (Engler et al. (2002) J Allergy Clin Immunol. 110:357-365). Thus, vaccination is contraindicated for people with AIDS or allergic skin diseases (Engler et al.). While protective immunity lasts for many years, the antibody response to smallpox vaccination is significantly reduced 10 to 15 years post inoculation (Downie, supra). In addition, vaccination may not be protective against recombinant forms of orthopoxvirus. A recent study showed that recombinant forms of mousepox virus that express IL-4 cause death in vaccinated mice (Jackson, supra). Given the side effects associated with vaccination, contraindication of immunocompromised individuals, and inability to protect against recombinant strains of virus, better preventatives and/or new therapeutics for treatment of smallpox virus infection are needed.

Vaccinia virus immunoglobulin (VIG) has been used for the treatment of post-vaccination complications. VIG is an isotonic sterile solution of immunoglobulin fraction of plasma derived from individuals who received the vaccinia virus vaccine. It is used to treat eczema vaccinatum and some forms of progressive vaccinia. Since this product is available in limited quantities and difficult to obtain, it has not been indicated for use in the event of a generalized smallpox outbreak (Modlin, supra).

Cidofovir ([(S)-1-(3-hydroxy-2-phosphonylmethoxypropyl)cytosine] [HBMPC]) is a nucleoside analog approved for treatment of CMV retinitis in AIDS patients. Cidofovir has been shown to have activity in vitro against a number of DNA containing viruses including adenovirus, herpesviruses, hepadnaviruses, polyomaviruses, papillomaviruses, and orthopoxviruses (Bronson et al. (1990) Adv. Exp. Med. Biol. 278:277-83; De Clercq et al. (1987) Antiviral Res. 8:261-272; de Oliveira et al. (1996) Antiviral Res. 31:165-172; Snoeck et al. (2001) Clin Infect. Dis. 33:597-602). Cidofovir has also been found to inhibit authentic variola virus replication (Smee et al. (2002) Antimicrob. Agents Chemother. 46:1329-1335).

However, cidofovir administration is associated with a number of issues. Cidofovir is poorly bioavailable and must be administered intravenously (Laezari et al. (1997) Ann. Intern. Med. 126:257-263). Moreover, cidofovir produces dose-limiting nephrotoxicity upon intravenous administration (Lalezari et al.). In addition, cidofovir-resistance has been noted for multiple viruses. Cidofovir-resistant cowpox, monkeypox, vaccinia, and camelpox virus variants have been isolated in the laboratory by repeated passage in the presence of drug (Smee, supra). Cidofovir-resistance represents a significant limitation for use of this compound to treat orthopoxvirus replication. Thus, the poor bioavailability, need for intravenous administration, and prevalence of resistant virus underscores the need for development of additional and alternative therapies to treat orthopoxvirus infection.

In addition to viral polymerase inhibitors such as cidofovir, a number of other compounds have been reported to inhibit orthopoxvirus replication (De Clercq. (2001) Clin Microbiol. Rev. 14:382-397). Historically, methisazone, the prototypical thiosemicarbazone, has been used in the prophylactic treatment of smallpox infections (Bauer et al. (1969) Am. J Epidemiol. 90:130-145). However, this compound class has not garnered much attention since the eradication of smallpox due to generally unacceptable side effects such as severe nausea and vomiting. Mechanism of action studies suggest that methisazone interferes with translation of L genes (De Clercq (2001), supra). Like cidofovir, methisazone is a relatively non-specific antiviral compound and can inhibit a number of other viruses including adenoviruses, picornaviruses, reoviruses, arboviruses, and myxoviruses (Id.).

Another class of compounds potentially useful for the treatment of poxviruses is represented by inhibitors of S-adenosylhomocysteine hydrolase (SAH). This enzyme is responsible for the conversion of S-adenosylhomocysteine to adenosine and homocysteine, a necessary step in the methylation and maturation of viral mRNA. Inhibitors of this enzyme have shown efficacy at inhibiting vaccinia virus in vitro and in vivo (De Clercq et al. (1998) Nucleosides Nucleotides. 17:625-634.). Structurally, all active inhibitors reported to date are analogues of the nucleoside adenosine. Many are carbocyclic derivatives, exemplified by Neplanacin A and 3-Deazaneplanacin A. While these compounds have shown some efficacy in animal models, like many nucleoside analogues, they suffer from general toxicity and/or poor pharmacokinetic properties (Coulombe et al. (1995) Eur. J Drug Metab Pharmacokinet. 20:197-202; Obara et al. (1996) J Med. Chem. 39:3847-3852). It is unlikely that these compounds can be administered orally, and it is currently unclear whether they can act prophylactically against smallpox infections. Identification of non-nucleoside inhibitors of SAH hydrolase, and other chemically tractable variola virus genome targets that are orally bioavailable and possess desirable pharmacokinetic (PK) and absorption, distribution, metabolism, excretion (ADME) properties would be a significant improvement over the reported nucleoside analogues. In summary, currently available compounds that inhibit smallpox virus replication are generally non-specific and suffer from use limiting toxicities and/or questionable efficacies.

In U.S. Pat. No. 6,433,016 (Aug. 13, 2002) and U.S. Application Publication 2002/0193443 A1 (published Dec. 19, 2002) a series of imidodisulfamide derivatives are described as being useful for orthopoxvirus infections.

New therapies and preventatives are clearly needed for infections and diseases caused by orthopoxvirus infection.

The co-owned PCT publication WO 2004/112718 (published Dec. 29, 2004) discloses the use of di, tri, and tetracyclic acylhydrazide derivatives and analogs, as well as pharmaceutical compositions containing the same, for the treatment or prophylaxis of viral infections and diseases associated therewith, particularly those viral infections and associated diseases caused by the orthopoxvirus. The co-owned U.S. Patent publication 2008/0004452 (published Jan. 3, 2008) further discloses a process for producing ST-246. Finally, the co-owned PCT publication WO 2011/119698 discloses processes of preparing various crystalline forms of ST-246.

The amorphous form of ST-246 provides an advantage over crystalline forms by having a faster dissolution rate, achieving supersaturation, and thus allowing for the potential of reducing dosages and may also avoid food effect as well as reduce pharmacokinetic variability. Therefore, there is a need to develop an effective process of producing amorphous ST-246, in particular from crystalline forms.

SUMMARY OF THE INVENTION

The present invention provides a method for producing amorphous N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, said method comprising:

(a) heating a solid form of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide at a temperature sufficient to cause melting; and (b) cooling the melted form of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide and thus producing amorphous N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

The present invention also provides a method for producing an amorphous solid dispersion of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, said method comprising:

(a) preparing liquid a solution comprising N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, at least one polymer and a solvent; and (b) spray drying said liquid solution, thereby producing said amorphous solid dispersion.

The present invention further provides a method for producing an amorphous solid dispersion of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, said method comprising:

(a) preparing liquid a solution comprising N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, at least one polymer and a solvent; and (b) spray drying said liquid solution, thereby producing said amorphous solid dispersion.

BRIEF DESCRIPTION OF THE DRAWING

FIG. 1 shows XRPD diffractogram of the amorphous ST-246 and PEG-4000 solid dispersion as described in Example 7.

DETAILED DESCRIPTION OF THE INVENTION

Described herein are processes for producing ST-246. The chemical name for ST-246 is N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide and has the following formula:

ST-246

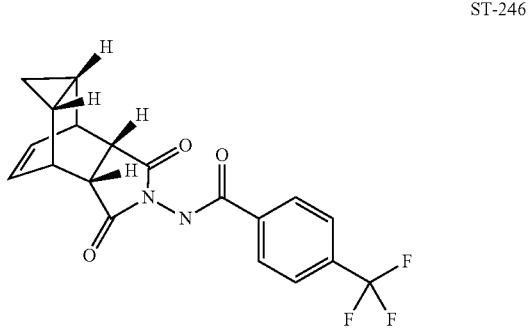

Definitions

In accordance with this detailed description, the following abbreviations and definitions apply. It must be noted that as used herein, the singular forms "a," "an," and "the" include plural referents unless the context clearly dictates otherwise.

The term "polymorphic form, polymorph, polymorph form, crystalline form, physical form or crystalline polymorph" of ST-246 in the present invention refers to a crystal modification of ST-246, which can be characterized by analytical methods such as X-ray powder diffraction pattern, (XRPD), differential scanning calorimetry (DSC), by its melting point analysis or Infrared Spectroscopy (FTIR) or polarized light microscopy.

The term "hydrate" as used herein means a compound or a salt thereof that further includes a stoichiometric or non-stoichiometric amount of water bound by non-covalent intermolecular forces. Hydrates are formed by the combination of one or more molecules of water with one molecule of the substances in which the water retains its molecular state as $H_2O$, such combination being able to form one or more hydrate. The term "hemihydrate" as used herein refers to a solid with 0.5 molecule of $H_2O$ per molecule of the substance.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

PCT publication WO 2011/119698 discloses 6 polymorphs or crystal structures for ST-246 with various degrees of hydration. As discussed above, the amorphous form of ST-246 is more desirable than crystalline forms because it has a faster dissolution rate and can achieve supersaturated concentrations. Accordingly, it has now been discovered that amorphous ST-246 can be prepared by heating solid or crystal forms of ST-246 at a temperature sufficient to cause melting followed by rapid cooling. The melting temperature of ST-246 is about 196° C.

Preferably, the heating of the solid or crystal forms of ST-246 is carried out at a temperature of at least about 196° C. and up to about 230° C. to minimize any thermal degradation of ST-246.

Also preferably, the cooling step of the melted ST-246 is carried out at a temperature below about 0° C., more preferably at a temperature of less than about −50° C., most preferably in liquid nitrogen.

Again preferably, the starting material of ST-246 comprises a polymorph such as a monohydrate polymorph. Examples of such polymorph hydrates include polymorph Form I of ST-246 which shows an X-ray powder diffraction pattern having characteristic peaks at a reflection angle 2θ of about 7.63,10.04,11.47,14.73,15.21,15.47,16.06,16.67, 16.98,18.93,19.96,20.52,20.79,22.8 0,25.16,26.53,27.20, 27.60,29.60,30.23,30.49,30.68,31.14,33.65,34.33,35.29, 35.56,3 6.30,37.36,38.42,38.66 degrees and a polymorph Form III of ST-246 which shows an X-ray powder diffraction pattern having characteristic peaks at a reflection angle 2θ of about 6.71,9.05,12.49, 13.03, 13.79, 14.87, 15.72, 16.26, 16.74, 18.10, 18.43,19.94,21.04,21.51,23.15,23.51, 25.32,26.24,26.87,27.32,27.72,28.55,29.08,29. 50,29.84, 31.27,33.48, 35.36,39.56 degrees.

It has also been discovered that an amorphous solid dispersion of N-[(3aR,4R,4aR,5aS,6S,6aS)-3,3a,4,4a,5,5a, 6,6a-octahydro-1,3-dioxo-4,6-ethenocycloprop[f]isoindol-2 (1H)-yl]-4-(trifluoromethyl)-benzamide can be prepared by: (a) preparing liquid a solution comprising N-[(3aR,4R,4aR, 5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, at least one polymer and a solvent; and (b) spray drying said liquid solution, thereby producing said amorphous solid dispersion. Typical instrument used for spray drying are commercially available and include but are not limited to Buchi B290 made by Buchi Corporation.

Preferably, the liquid solution comprises at least one solvent selected from the group consisting of: tetrahydrofuran, ethyl alcohol, ethyl acetate, methyl ether ketone, dichloromethane, water and mixtures thereof. More preferably, the solvent is tetrahydrofuran, methanol or acetone.

Also preferably, the polymer is selected from the group consisting of: methacrylic acid coplolymer, Hydroxypropyl methyl cellulose (HPMC), HPMCP-H55, CAP, PVAP, HPMCAS-L, HPMCAS-M, HPMCAS-H, Hypromellose, Povidone, Copovidone, HPC, Poloxamer, PVP-VA, PVP (neutral), Klucel, Methocel, Ethocel, Plasdone, and mixtures thereof. More preferably, the polymer is (Hydroxypropyl) methyl cellulose and Hydroxypropyl methyl cellulose acetate succinate.

Again preferably, the liquid solution comprises a surfactant. More preferably, the surfactant is selected from the group consisting of: Polysorbate, Cremophor and Kolliphor.

Also preferably, the ratio by weight of N-[(3aR,4R,4aR, 5aS,6S,6aS)-3,3a,4,4a,5,5a,6,6a-octahydro-1,3-dioxo-4,6- ethenocycloprop[f]isoindol-2(1H)-yl]-4-(trifluoromethyl)-benzamide to the polymer in said solution is from about 1:50 to about 1:1, more preferably about 1:9 or about 1:2.

It has further been discovered that an amorphous solid dispersion of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide can be prepared by: (a) heating a solid form of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide in the presence of at least one polymer at a temperature sufficient to cause melting and produce a liquid solution; and (b) cooling the solution of step (a) and thus producing said amorphous dispersion.

Preferably, the polymer is selected from the group consisting of: Polyethylene glycol, Gelucire, Glycerol mono and di stearate, methacrylic acid copolymer, Hydroxypropyl methyl cellulose (HPMC), HPMCP-H55, CAP, PVAP, HPMCAS-L, HPMCAS-M, HPMCAS-H, Hypromellose, Povidone, Copovidone, HPC, Poloxamer, PVP-VA, PVP (neutral), Klucel, Methocel, Ethocel, Plasdone, and mixtures thereof. More preferably, the polymer is Polyethylene glycol.

Again preferably, the liquid solution comprises a surfactant. More preferably, the surfactant is selected from the group consisting of: Polysorbate, Cremophor and Kolliphor.

Also preferably, the ratio by weight of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide to the polymer in said solution is from about 1:50 to about 1:1, more preferably about 1:9 or about 1:2.

Also preferably, the cooling step of the melted ST-246 is carried out at a temperature below about 0° C., more preferably at a temperature of less than about −50° C., most preferably in liquid nitrogen.

The present invention also provides a pharmaceutical composition comprising a purified or isolated amorphous N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide and further comprising one or more pharmaceutically acceptable ingredients selected from the group consisting of carriers, excipients, diluents, additives, fillers, lubricants and binders, wherein at least 90%, preferably at least 95% of said N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide is amorphous. Preferably, the pharmaceutical composition is formulated for oral administration.

The present invention further provides a method of treating Orthopoxvirus infections or eczema vaccinatum comprising administering to a patient in need thereof a therapeutically effective amount of a purified amorphous N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, wherein at least 90%, preferably at least 95% of said N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide is amorphous.

Formulations and Administration

Formulations of amorphous ST-246 may be prepared by processes known in pharmaceutics art. The following examples (infra) are given to enable those skilled in the art to more clearly understand and to practice the present invention. They should not be considered as limiting the scope of the invention, but merely as being illustrative and representative thereof.

The amorphous salts of the present invention can be administered in a variety of oral and parenteral dosage forms. Oral dosage forms can be tablets, coated tablets, hard and soft gelatin capsules, solutions, emulsions, syrups, or suspensions. Parenteral administration includes intravenous, intramuscular, intracutaneous, subcutaneous, intraduodenal, or intraperitoneal administration. Additionally, the salts of the present invention can be administered by transdermal (which may include a penetration enhancement agent), buccal, nasal and suppository routes.

For preparing pharmaceutical compositions from the compounds of the present invention, pharmaceutically acceptable carriers can be either solid or liquid. Solid form preparations include powders, tablets, pills, hard and soft gelatin capsules, cachets, suppositories, and dispersible granules. A solid carrier can be one or more substances which may also act as diluents, flavoring agents, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

Suitable excipients for tablets, coated tablets, and hard gelatin capsules are, for example, microcrystalline cellulose, lactose, corn starch and derivatives thereof, magnesium carbonate, magnesium stearate, sugar, lactose, pectin, dextrin, starch, gelatin, tragacanth, methylcellulose, sodium carboxymethylcellulose, talc, and fatty acids or their salts, e.g., stearic acid. If desired, the tablets or capsules may be enteric-coated or sustained release formulations. Suitable excipients for soft gelatin capsules are, for example, vegetable oils, waxes, fats, semi-solid and liquid polyols. Liquid form preparations include solutions, suspensions, retention enemas, and emulsions. For parenteral injection, liquid preparations can be formulated in solution in water or water/polyethylene glycol solution.

Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Compositions also may contain, in addition to the active component, colorants, flavors, stabilizers, buffers, artificial and natural sweeteners, dispersants, thickeners, preservatives, wetting agents, emulsifiers, salts for adjustment of the osmotic pressure, masking agents, antioxidants and the like.

The compounds of the present invention can be administered intravenously in physiological saline solution (e.g., buffered to a pH of about 3 to 8). Conventional buffers such as phosphates, bicarbonates or citrates can be used in the present compositions.

Also included are solid form preparations which are intended to be converted, shortly before use, to liquid form preparations for oral administration. Such liquid forms include solutions, suspensions, and emulsions. For preparing suppositories suitable excipients include natural and hardened oils, waxes, fatty acid glycerides, semi-liquid or liquid polyols. The molten homogenous mixture is then poured into convenient sized molds, allowed to cool, and thereby to solidify. Suitable pharmaceutical carriers, excipients and their formulations are described in Remington: The Science and Practice of Pharmacy 1995, edited by E. W. Martin, Mack Publishing Company, 19th edition, Easton, Pa.

The dosage can vary within wide limits and will, of course, be adjusted in each particular case to the individual requirements of the patient and the severity of the condition being treated. A typical preparation will contain from about 5% to about 95% active compound (w/w). For oral administration, a daily dosage of between about 0.01 and about 100 mg/kg body weight per day should be appropriate in monotherapy and/or in combination therapy. A preferred daily dosage is between about 0.1 and about 300 mg/kg body weight, more preferred 1 and about 100 mg/kg body weight and most preferred 1.0 and about 50 mg/kg body weight per day.

Generally, treatment is initiated with smaller dosages which are less than the optimum dose of the compound. Thereafter, the dosage is increased by small increments until the optimum effect under the circumstance is reached. The daily dosage can be administered as a single dosage or in divided dosages, typically between 1 and 5 dosages per day.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Appropriate doses will be readily appreciated by those skilled in the art. It will be appreciated that the amount of a polymorph of the invention required for use in treatment will vary with the nature of the condition being treated and the age and the condition of the patient and will be ultimately at the discretion of the attendant physician or veterinarian. The polymorph of the invention may be used in combination with other antibacterial drugs such as penicillin, cephalosporin, sulfonamide or erythromycin.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the amorphous ST-246 compound of the invention or the second therapeutic agent may be administered first. When administration is simultaneous, the combination may be administered either in the same or different pharmaceutical composition.

Using the routes and methods of administration and dosage amounts described hereinabove and the dosage forms described herein below, the amorphous form of ST-246 of the present invention can be used for the prevention and treatment of various diseases and conditions in humans. By way of example and not of limitation, in the case of orthopoxvirus infections and associated diseases, this is accomplished by administering to a patient in need of said treatment who is suffering from orthopoxvirus infections a composition containing amorphous ST-246, substantially free of polymorph forms or mixtures of polymorphs and an inert carrier or diluent, said composition being administered in an effective amount to prevent or treat said viral infection.

In accordance with this invention, amorphous ST-246 substantially free of polymorph forms or as a mixture of polymorph forms, is administered in an effective amount to prevent or treat orthopoxviral infection. Any effective amount of such amorphous form substantially free of polymorph forms or mixtures of polymorph forms needed to prevent or treat such viral infection can be utilized in this composition. In general, in the case oral dosage forms, dosages of from about 0.5 mg/kg to about 5.0 mg/kg of body weight per day are used. However the amount of such amorphous form, substantially free of polymorph forms or mixtures of polymorph forms in the oral unit dose to be administered will depend to a large extent on the condition of viral infection, and the weight of the patient and of course be subject to the physician's judgment.

In accordance with this invention, the oral unit dosage form containing the given amorphous form substantially free of polymorph forms or mixtures of polymorph forms can be preferably administered at a dosage of from about 30 mg to 800 mg per day, more preferably from about 50 mg to about 600 mg per day, most preferably about 300 mg or 400 mg per day, administered once to three times during the day or as needed.

In some aspect of the invention, the amorphous form of the present invention may also be used in combination with: (1) a vaccine (2) Cidofovir, an injectable antiviral medication which is acyclic nucleoside phosphonate, and is therefore independent of phosphorylation by viral enzymes, to treat eczema vaccinatum (EV), a life-threatening complication of vaccinia virus infection, and other related disorders; and/or (3) CMX001 (hexadecyloxypropyl-cidofovir), a mimic of a naturally occurring lipid, lysolecithin, formed by linking a lipid, 3-hexadecyloxy-1-propanol, to the phosphonate group of cidofovir.

The invention also provides pharmaceutical packs or kits comprising one or more containers filled with the amorphous form of ST-246. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLE 1

Preparation of Amorphous ST-246 by Melting and Quench Cooling

Approximately 20 g ST-246 monohydrate (polymorph Form I) was dehydrated in a desiccator with Drierite under vacuum in a drying oven at 50° C. for 2 days to yield dehydrated ST-246.

In a glove box under a nitrogen atmosphere (RH<5%), 5.2 g dehydrated ST-246 was weighed into a beaker and was heated in a silicone oil bath with bath temperature maintained at 215° C. and held for 5 minutes or until material is completely melted, The beaker was removed from the silicone oil bath and was quenched immediately by immersing in liquid nitrogen. The beaker was held in liquid nitrogen for 1 minute, then immediately transferred to a glove box under a nitrogen atmosphere (RH<5%). Product was transferred from the glass beaker to an 10 mL amber glass bottle and sealed with PTFE lined cap. It was stored in a freezer at −20° C. Product was pale yellow in color, The yield was 5.1 g.

The quench cooled ST-246 was characterized using the following analyses: Water content by Karl Fischer titration, polarized light microscopy, purity by HPLC, and XRPD. Moisture content of the Product was measured at 0.09%. A sample of final product showed no birefringence under polarized light, indicating product is amorphous. The purity was 99.1% by HPLC (area% at 224 nm). Finally, the XRPD diffractogram showed a halo pattern with no peaks, indicating the product is amorphous.

EXAMPLE 2

Preparation of Amorphous ST-246 by Melting

About 5.0 g ST-246 monohydrate was weighed into a 25 mL Pyrex test tube and placed in a silicone oil bath at ambient temperature. The silicone oil bath was heated to 210° C. over the course of 2 hours. Low flow nitrogen was delivered to the test tube using Tygon tubing during the heating process. When oil bath temperature reached 202° C., the ST-246 began to melt. ST-246 melted to a clear colorless liquid when the oil bath temperature reached 210° C. ST-246 was then removed from the heat and the test tube was immediately placed in an ice bath and held for 5 minutes while continuing to blow low flow nitrogen into the test tube. It was then removed from ice bath and transferred to a glove box under nitrogen atmosphere (<10% RH). The product was then transferred to an amber glass bottle sealed with PTFE lined cap. It was stored in a freezer at −20° C. The product was a glassy colorless solid.

The product was analyzed for purity, which was 97.9% by HPLC.

EXAMPLE 3

Preparation of Amorphous ST-246 by Melting and Quench Cooling

About 2.00 g of ST-246 monohydrate were added to a steel beaker and placed in a silicone oil bath at room temperature. The oil bath was heated and stirred using a stirring hot plate. The heated oil bath temperature reached 160° C. over the course of 2 hours followed by an increase to 205° C. over 25 minutes. ST-246 began to slowly melt when bath temperature reached 205° C. The bath temperature was then raised to 215° C. over the next 20 minutes. ST-246 was completely melted when the oil bath temperature reached 215° C. The beaker was then from the oil bath and placed in liquid nitrogen and held for approximately 1 minute. The product inside the beaker was yellow in color and immediately hardened. The beaker containing the product was then placed in a glove box under a nitrogen atmosphere (relative humidity less than 10%). The product was then transferred to an amber glass bottle and sealed with PTFE lined cap. The Yield was 1.8 g of product. The product was a yellow colored glass. It was stored in a freezer at −20° C. The purity was 98.1% by HPLC (area% at 224 nm). The XRPD diffractogram showed a halo pattern with no peaks, indicating the product is amorphous.

EXAMPLE 4

Preparation of Amorphous ST-246 Spray Dried Dispersion with PVP

About 2.0 g ST-246 monohydrate and 4.0 g Kollidon 30 (PVP) were dissolved in 45 mL methanol. Spray dried resulting solution using a Buchi B290 mini-Spray Dryer and Buchi B-295 Intert Loop, set to the following parameters:

Aspirator: 100%; Nitrogen flow: 30 $m^3$/hr; Feed rate: 30%; and Inlet temp: 65° C.

The resulting product was a white fluffy powder. The purity was 99.9% by HPLC (area% at 224 nm). The product was then transferred to an amber glass bottle sealed with PTFE lined cap. It was stored in a freezer at −20° C. The XRPD diffractogram showed a halo pattern with no peaks, indicating the product is amorphous.

EXAMPLE 5

Preparation of Amorphous ST-246 Spray Dried Dispersion with HPMCAS-M

About 0.50 g ST-246 monohydrate and 4.50 g HPMCAS-M were dissolved in about 300 mL of 95:5 THF:water (v/v). The solution was then spray dried using a Buchi B290 mini-Spray Dryer and Buchi B-295 Intert Loop, set to the following parameters:

Aspirator: 100%; Nitrogen flow: 40 $m^3$/hr; Feed rate: 40%; and Inlet temp: 60° C.

The Product was a white fluffy powder having a purity of 99.8% by HPLC (area% at 224 nm). The product was then transferred to an amber glass bottle sealed with PTFE lined cap. It was stored in a freezer at −20° C. The XRPD diffractogram showed a halo pattern with no peaks, indicating the product is amorphous.

EXAMPLE 6

Preparation of Amorphous ST-246 Spray Dried Dispersion with HPMC

About 4.50 g (Hydroxypropyl) methyl cellulose (viscosity 2600-5600 cp) was dissolved in about 400 mL THF 100m1 of water. In a separate flask, about 0.50 g ST-246 monohydrate was dissolved in 10 mL THF. The ST-246 solution was added to the HPMC solution. The resulting solution was spray dried using a Buchi B290 mini-Spray Dryer and Buchi B-295 Inert Loop, set to the following parameters:

Aspirator: 100%; Nitrogen flow: 40 $m^3$/hr; Feed rate: 40%; and Inlet temp: 65° C.

The product was a white fluffy powder having a purity of 99.8% by HPLC (area % at 224 nm). The product was then transferred to an amber glass bottle sealed with PTFE lined cap. It was stored in a freezer at −20° C. The XRPD diffractogram showed a halo pattern with no peaks, indicating the product is amorphous.

EXAMPLE 7

Preparation of Amorphous ST-246 by Hot Melt Extrusion (HMS) with PEG-4000

About 4.0 g Poly(ethylene glycol) m.w. 4000 were transferred into a 125 mL steel beaker and placed with stirring on a stirring hot plate set to 150° C. PEG4000 melted rapidly. About 1.0 g ST-246 monohydrate was then added and stirring was continued while covered for 10 minutes. Thereafter, the temperature was raised to 175° C. After 30 minutes of stirring at 175° C. a clear solution was obtained. The solution was removed from the heat and immediately placed in a beaker in liquid nitrogen and held for approximately 2 minutes.

The product was a white translucent glass having a purity of 99.7% by HPLC (area % at 224 nm). The product was then transferred to an amber glass bottle sealed with PTFE lined cap. It was stored in a freezer at −20° C. The XRPD diffractogram of FIG. 1 showed highly defected peaks, indicating the product is a disordered crystalline material or mesophase.

All references cited herein are herein incorporated by reference in their entirety for all purposes.

The invention has been described in terms of preferred embodiments thereof, but is more broadly applicable as will be understood by those skilled in the art. The scope of the invention is only limited by the following claims.

What is claimed is:

1. A method for producing an amorphous solid dispersion of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, said method comprising:
   (a) preparing a liquid solution comprising N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, at least one polymer and a solvent; and
   (b) spray drying said liquid solution, thereby producing said amorphous solid dispersion.

2. The method of claim 1, wherein said liquid solution comprises at least one solvent selected from the group consisting of tetrahydrofuran, alcohol, ethyl acetate, acetone, methoxy acetone (methyl ether ketone), dichloromethane, and water, or mixtures thereof.

3. The method of claim 2, wherein said solvent is tetrahydrofuran.

4. The method of claim 2, wherein said solvent is methanol or acetone.

5. The method of claim 1, wherein said polymer is selected from the group consisting of methacrylic acid copolymer, Hydroxypropyl methyl cellulose (HPMC), HPMCP-H55, CAP, PVAP, HPMCAS-L, HPMCAS-M, HPMCAS-H, Hypromellose, HPC, Poloxamer, PVP VA, PVP(neutral), hydroxypropyl cellulose, methyl cellulose, and ethyl cellulose, or mixtures thereof.

6. The method of claim 5, wherein said polymer is (Hydroxypropyl) methyl cellulose acetate succinate (HPMCAS).

7. The method of claim 1, wherein said liquid solution comprises a surfactant.

8. The method of claim 7, wherein said surfactant is selected from the group consisting of Polysorbate, and polyoxyethylated triglycerides.

9. The method of claim 1, wherein the ratio by weight of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide to the polymer in said solution is from about 1:50 to about 1:1.

10. The method of claim 1, wherein the ratio by weight of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide to the polymer in said solution is about 1:9.

11. The method of claim 1, wherein the ratio by weight of N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide to the polymer in said solution is about 1:2.

* * * * *

UNITED STATES PATENT AND TRADEMARK OFFICE
CERTIFICATE OF CORRECTION

PATENT NO. : 9,889,119 B2
APPLICATION NO. : 15/498787
DATED : February 13, 2018
INVENTOR(S) : Shanthakumar R. Tyavanagimatt et al.

It is certified that error appears in the above-identified patent and that said Letters Patent is hereby corrected as shown below:

On the Title Page

Item (60) Provisional Application Number should be corrected to read:
--61/856,240--

Signed and Sealed this
Twentieth Day of March, 2018

Andrei Iancu
*Director of the United States Patent and Trademark Office*